United States Patent [19]

Lednicer et al.

[11] 4,212,878
[45] Jul. 15, 1980

[54] PHENYLACETAMIDE DERIVATIVE ANALGESICS

[75] Inventors: Daniel Lednicer, Evansville, Ind.; Jacob Szmuszkovicz, Kalamazoo, Mich.

[73] Assignee: The Upjohn Company, Kalamazoo, Mich.

[21] Appl. No.: 872,632

[22] Filed: Jan. 26, 1978

[51] Int. Cl.$^2$ .................. C07D 405/04; A61K 31/40; C07D 207/04
[52] U.S. Cl. .............................. 424/274; 260/239 A; 260/326.36; 260/326.4; 260/340.7; 260/340.9 R; 260/349; 260/559 A; 260/559 R; 424/244; 424/278; 424/320
[58] Field of Search ........... 260/326.4, 326.36, 559 R, 260/559 A, 340.7, 340.9 R, 239 A; 546/197, 234; 424/274, 278, 244, 320

[56] References Cited

U.S. PATENT DOCUMENTS

| | | | |
|---|---|---|---|
| 3,975,443 | 8/1976 | Harper et al. | 260/559 |
| 4,049,663 | 9/1977 | Harper | 544/197 |
| 4,065,573 | 12/1977 | Lednicer | 424/278 |
| 4,098,904 | 7/1978 | Szmuszkovicz | 260/326.4 |
| 4,152,459 | 5/1979 | Szmuszkovicz | 260/326.4 |
| 4,156,733 | 5/1979 | Szmuszkovicz | 260/326.4 |

OTHER PUBLICATIONS

Harper et al.; J. Med. Chem. vol. 17, pp. 1188–1193 (1974).
Buttain et al.; But. Pharm. Soc. Proceeding pp. 158p–159p (1973).

Primary Examiner—Mary C. Lee
Attorney, Agent, or Firm—John T. Reynolds

[57] ABSTRACT

N-[(1-Amino-4-(mono or di-oxygen-group-substituted)-cyclohex-1-yl)methyl]phenylacetamide derivatives of the formula 1

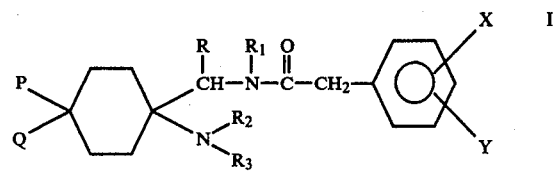

wherein R, R$_1$, R$_2$, R$_3$, P, Q, X and Y are defined in the specification, e.g., 2-(3,4-dichlorophenyl)-N-[[8-(1-pyrrolidinyl)-1,4-dioxaspiro[4.5]dec.-8-yl]methyl]acetamide, and their pharmacologically acceptable salts, have analgesic drug properties with lower physical dependence liability characteristics than morphine or methadone, for use as analgesic drugs in mammalian animals including humans.

18 Claims, No Drawings

PHENYLACETAMIDE DERIVATIVE ANALGESICS

INTRODUCTION

This invention relates to some phenylacetamide derivative compounds. More particularly, this invention provides some new N-[(4-mono- or di-oxygen-group-substituted-1-aminocyclohex-1-yl)methyl]-phenylacetamides which have been found to have potent analgesic properties and reduced physical dependence liability properties, relative to morphine and methadone.

BACKGROUND OF THE INVENTION

R. T. Brittain et al., in *Brit. J. Pharm.*, 49, 158 (1973) and N. J. Harper et al., in *J. Med. Chem.*, 17, 1188 (1974), disclose some 1-amino-1-benzamidomethylcyclohexane analgesic compounds of the formulae:

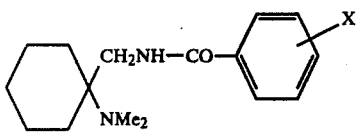

wherein X is hydrogen, 4-F, 3,4-di-Cl, 2-Cl, 3-Cl or 4-Cl and Me donotes methyl;

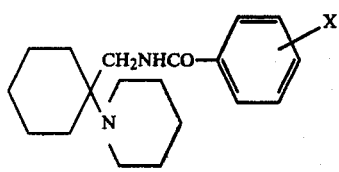

where X is 4-fluoro, 3,4-dichloro or 2-chloro or 4-chloro; and

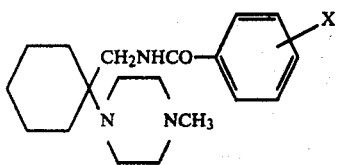

where X is hydrogen or 3,4-dichloro, but such compounds are not acetamides as are the compounds of this invention.

Also, Harper et al., in U.S. Pat. No. 3,975,443, in which numerous patent and other publication references are cited, discloses a class of compounds of the formula

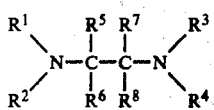

but claims only 1-(3,4-dichlorobenzamidomethyl)- cyclohexyldimethylamine. These compounds are stated to have utility as oral analgesics.

In addition, Lednicer U.S. application Ser. No. 692,589, filed June 3, 1976, now U.S. Pat. No. 4,065,573, issued Dec. 26, 1978, discloses analgesic compounds of the formula

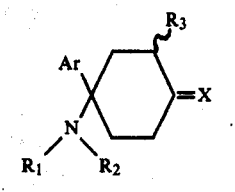

wherein X is oxo or

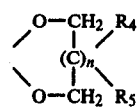

wherein n is zero or 1, $R_4$ is hydrogen or methyl, $R_5$ is hydrogen, phenyl, —$CH_2$-alkenyl wherein alkenyl is of 2 to 4 carbon atoms, inclusive, or methyl; aryl (Ar—) is thiophene or

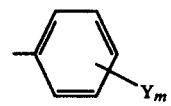

wherein m is zero, one or two, and Y is halogen, $CF_3$, $C_1$ to $C_4$-alkyl, $C_1$ to $C_4$-alkoxy, hydroxy, $C_3$ to $C_6$-cycloalkyloxy, $C_2$ to $C_4$-alkanoyloxy, $C_1$ to $C_4$-alkylthio, or

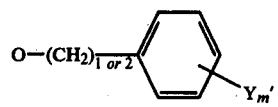

wherein Y' is halogen, —$CF_3$, $C_1$ to $C_4$-alkyl, $C_1$ to $C_4$-alkyloxy, $R_1$ is hydrogen, $C_1$ to $C_8$-alkyl, $R_2$ is hydrogen, $C_1$ to $C_8$-alkyl, —$CH_2$-alkenyl wherein alkenyl is 2 to 8 carbon atoms, acetyl, cycloalkylalkyl having 3 to 6 carbons in the cycloalkyl and 1 to 3 carbons in the alkyl, β-hydroxyethyl, carbethoxymethyl, $C_3$ to $C_6$-cycloalkyl,

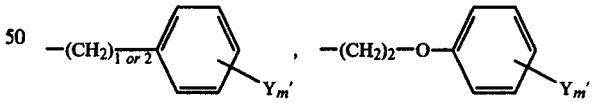

and $R_3$ is hydrogen, $C_1$ to $C_5$-alkyl, and the acid addition salts thereof, among others. However, such compounds do not have geminal 1-amino-1-amidomethyl substituents similar to those described and claimed herein.

OBJECTS OF THE INVENTION

It is an object of this invention to provide some new and useful phenylacetamide derivative compounds.

It is a further object of this invention to provide some new phenylacetamide derivative compounds which have useful analgesic drug properties with reduced physical dependence liability properties, which can also be used as antitussives.

It is an object of this invention to provide new pharmaceutical formulation compositions and a method for reducing pain in mammals using the new compounds of this invention.

Other objects, aspects and advantages of this invention will become apparent from the remaining specification and the claims which follow.

SUMMARY OF THE INVENTION

Briefly, this invention provides some N-[(4-mono- or di-oxygen-group-substituted-1-aminocyclohex-1-yl)methyl]phenylacetamides, e.g., 2-(3,4-dichlorophenyl)-N-[[8-(1-pyrrolidinyl)-1,4-dioxaspiro[4,5]-dec.-8-yl]methyl]acetamide, and their pharmacologically acceptable salts as new compounds, which have been found to have potent analgesic properties as well as reduced physical dependence liability properties. This invention also provides pharmaceutical formulations containing these new compounds as an active analgesic ingredient and a method for reducing pain in mammalian animals by administering to the mammalian patient a pharmaceutical formulation containing one of these compounds in an amount effective to reduce the pain or discomfort (e.g., cough).

DETAILED DESCRIPTION OF THE INVENTION

This invention provides compounds of the formula I

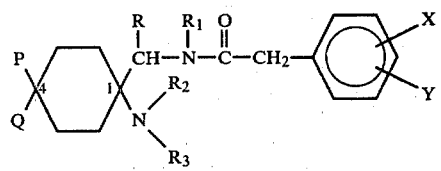

wherein
R is hydrogen or $C_1$ to $C_3$-alkyl;
$R_1$ is hydrogen or $C_1$ to $C_3$-alkyl;
each of $R_2$ and $R_3$ is independently a $C_1$ to $C_6$-alkyl, or $R_2$ is a $C_3$ to $C_5$-(allylic)alkenyl when $R_3$ is $C_1$ to $C_6$-alkyl, or $R_2$ and $R_3$ taken together with the nitrogen to which they are bonded complete a mono-nitrogen heterocyclic ring having from 3 to 4 ring carbon atoms and no other hetero-atoms in the ring;
Q and P taken together represent an oxo (O=) group or a $C_2$ to $C_3$-alkylenedioxy group, that is, a group of the formula

where n is 2 to 3; and, taken separately, when P or Q is hydroxy, then the other of Q or P is hydrogen, $C_1$ to $C_3$-alkyl, or phenylalkyl with alkyl being of 1 to 2 carbon atoms;
each of X and Y is selected from the group consisting of hydrogen, $C_1$ to $C_3$-alkyl, $C_1$ to $C_3$-alkyloxy, a halogen having an atomic number of from 9 to 35, nitro, trifluoromethyl, and azido, providing that when X is halogen, Y is $C_1$ to $C_3$-alkyl, $C_1$ to $C_3$-alkyloxy or halogen and that when X is nitro, trifluoromethyl or azido, Y is hydrogen, and the pharmacologically acceptable salts thereof.

A preferred subgroup of compounds of the above type are those wherein R is hydrogen, $R_1$ is hydrogen, $R_2$ and $R_3$ are taken together with the nitrogen to which they are bonded to complete a mono-nitrogen heterocyclic ring having from 3 to 4 carbon atoms; Q and P, taken together, complete a $C_2$ to $C_3$-alkylenedioxy group; and
X and Y are halogens having an atomic number of from 9 to 35, preferably in the 3- and 4-positions of the phenyl ring, and the pharmacologically acceptable salts thereof. Examples of such compounds include:
2-(3,4-dichlorophenyl)-N-[[8-(1-pyrrolidinyl)-1,4-dioxaspiro[4.5]dec-8-yl]methyl]acetamide, which can also be named N-[[1-(N-pyrrolidinyl)-4-oxocyclohex-1-yl]methyl]-2-(3,4-dichlorophenyl)acetamide, ethylene ketal,
2-(3,4-dichlorophenyl)-N-[[8-(1-azetidinyl)-1,4-dioxaspiro[4.5]dec-8-yl]methyl]acetamide,
2-(3,4-difluorophenyl)-N-[[8-(1-azetidinyl)-1,4-dioxaspiro[4.5]dec-8-yl]methyl]acetamide,
2-(3,4-dibromophenyl)-N-[[9-(1-pyrrolidinyl)-1,5-dioxaspiro[5.5]undec-9-yl]methyl]acetamide, and the like, and the pharmacologically acceptable salts thereof.

Another useful subgroup of compounds within the scope of this invention is that of formula I above where R is hydrogen, $R_1$ is hydrogen, $R_2$ and $R_3$ are each $C_1$ to $C_6$-alkyl, P and Q are taken together to complete a $C_2$ to $C_3$-alkylenedioxy group, and each of X and Y is a halogen having an atomic number of from 9 to 35, and the pharmacologically acceptable salts thereof. Examples of these types of compounds are 2-(3,4-dichlorophenyl)-N-[[8-(N,N-dimethylamino)-1,4-dioxaspiro[4.5]dec-8-yl]methyl]acetamide and 2-(3,4-dichlorophenyl)-N-[[9-(N,N-dipropylamino)-1,5-dioxaspiro[5.5]undec-9-yl]methyl]acetamide,
2-(3,4-dichlorophenyl)-N-[[8-(diethylamino)-1,4-dioxaspiro[4.5]dec-8-yl]methyl]acetamide,
2-(3,4-dibromophenyl)-N-[[8-dipropylamino)-1,4-dioxaspiro[4.5]dec-8-yl]methyl]acetamide,
2-(3,4-dichlorophenyl)-N-[[8-(N-methyl-N-butyl)-1,4-dioxaspiro[4.5]dec-8-yl]methyl]acetamide,
and the acid addition salts thereof.

Another useful subgroup of compounds of formula I is that wherein R is hydrogen, $R_1$ is hydrogen, $R_2$ is $C_3$ to $C_5$-(allylic)alkenyl, $R_3$ is $C_1$ to $C_6$-alkyl, P and Q, taken together, complete a $C_2$ to $C_3$ alkylenedioxy group, and X and Y are each halogens having an atomic number of from 9 to 35, and the pharmacologically acceptable salts thereof. An example is N-[[8-(N-allyl-N-methylamino)-1,4-dioxaspiro-[4.5]dec-8-yl]methyl]-2-(3,4-dichlorophenyl)acetamide, and the pharmacologically acceptable salts thereof.

Another useful subgroup of compounds of formula I is that wherein R is hydrogen, $R_1$ is hydrogen, $R_2$ and $R_3$ are taken together with nitrogen to which they are bonded to complete a mono-nitrogen heterocyclic ring having three to four carbon atoms, P and Q, taken together, complete a $C_2$ to $C_3$-alkylenedioxy group, X is a halogen having an atomic number of from 9 to 35 and Y is $C_1$ to $C_3$-alkyloxy group, and the pharmacologically acceptable salts thereof. An example of this type of compound is 2-(3-bromo-4-methoxyphenyl)-N-[[8-(pyrrolidinyl)-1,4-dioxaspiro-[4.5]dec-8-yl]methyl]acetamide, and the pharmacologically acceptable salts thereof.

Another useful subgroup of compounds of formula I is that wherein R and $R_1$ are hydrogen, $R_2$ and $R_3$ each are $C_1$ to $C_6$-alkyl, P is hydroxy and Q is phenyl-$C_1$-$C_2$-alkyl, and each of X and Y is a halogen having an atomic number of from 9 to 35, and the pharmacologically acceptable salts thereof. Examples of this type of compound include 2-(3,4-dichlorophenyl)-N-[(4-hydroxy-4-benzyl-1-dimethylaminocyclohex-1-yl)methyl]acetamide, and 2-(3,4-dichlorophenyl)-N-[(4-hydroxy-4-benzyl-1-methylbutylaminocyclohex-1-yl)methyl]acetamide, and the pharmacologically acceptable salts thereof.

Additional useful compounds within formula I include:

N-[(1-azetidinyl)-4-oxocyclohex-1-yl)methyl]-2-(4-azidophenyl)acetamide, 2-(3,4-dichlorophenyl)-N-[[9-(1-azetidinyl)-1,5-dioxaspiro[5.5]undec-9-yl]methyl]acetamide N-[[1-(N,N-diethylamino)-4-oxocyclohex-1-yl]methyl]-2-(4-trifluoromethylphenyl)acetamide, N-methyl-N-[[9-(N,N-dipropyl)-1,5-dioxaspiro-[5.5]undec-9-yl]methyl]-2-(3-nitrophenyl)acetamide, 2-(4-azidophenyl)-N-[[9-(N-methyl-N-ethylamino)-1,5-dioxaspiro[5.5]undec-9-yl]methyl]acetamide, 2-(3-trifluoromethylphenyl)-N-methyl-N-[[8-(dimethylamino)-1,4-dioxaspiro[4.5]dec-8-yl]-methyl]acetamide, 2-(3-chloro-4-methylphenyl)-N-[α-[8-(dimethylamino)-1,4-dioxaspiro[4.5]dec-8-yl]ethyl]acetamide, 2-(3-trifluoromethylphenyl)-N-[[8-(1-pyrrolidinyl)-1,4-dioxaspiro[4.5]dec-8-yl]methyl]acetamide, 2-(2,4-difluorophenyl)-N-[[1-pyrrolidinyl)-4-oxocyclohex-1-yl]methyl]acetamide, 2-(4-methoxy-3-methyl)-N-[[8-(N-methyl-N-butylamino)-1,4-dioxaspiro[4.5]dec-8-yl]methyl]acetamide, 2-(3,4-dichlorophenyl)-N-methyl-N-[[8-(N-methyl-N-butyl)-1,4-dioxaspiro[4.5]dec-8-yl]methyl]acetamide, 2-(3,4-dichlorophenyl)-N-[[1-(1-pyrrolidinyl)-4-oxocyclohex-1-yl]methyl]acetamide, 2-(3,4-dichlorophenyl)-N-[[1-pyrrolidinyl)-4-hydroxy-4-methylcyclohex-1-yl]methyl]acetamide, 2-(3,4-dichlorophenyl)-N-[[1-(1-azetidinyl)-4-hydroxy-4-benzylcyclohex-1-yl]methyl]acetamide, 2-(3,4-dibromophenyl)-N-[α-[8-(1-pyrrolidinyl)-1,4-dioxaspiro[4.5]dec-8-yl]propyl]acetamide, 2-(3-chloro-4-ethoxyphenyl)-N-ethyl-N-[[8-(N,N-dimethylamino)-1,4-dioxaspiro[4.5]dec-8-yl]methyl]acetamide, and the pharmacologically acceptable salts thereof.

The final compounds of this invention (formula I) can be prepared by methods known in the art, two of which methods are set forth below in detail. In general, the new 1-amidomethyl-1-aminocyclohexyl compounds of this invention can be prepared by reacting the appropriate diamine of the formula

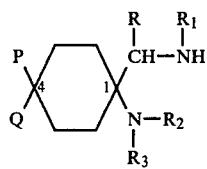

wherein R, R₁, R₂ and R₃ are as defined above and P and Q, taken together, represent an alkylenedioxy group as defined above with an aracylimidazole of the formula

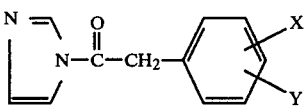

wherein X and Y are as defined above, or with an acyl halide of the formula

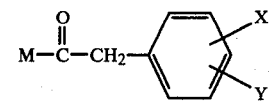

wherein M is chloride or bromide and X and Y are as defined above, in an organic solvent for the reactants, preferably an ether solvent such as diethyl ether, tetrahydrofuran, or the like, until the compound of this invention is produced. An excess of the aracylimidazole or the acyl halide reactant can be used to insure complete reaction of the more expensive diamine, although the aracylimidazole or acyl halide reactants can be mixed in substantially equal proportions to the diamine reactant to effect formation of the desired compound I. This reaction will proceed at an ambient temperature for most combinations of reactants but for some combinations of reactants, variations from the initial to final reaction conditions may vary between about −10° C. and reflux temperature of the mixture, depending upon the reactivity of the reactants, the desired reaction time, the solvent being used, and similar factors of concern to the chemist operating the process. When the reaction has proceeded to substantial completion, the product can be recovered and purified by conventional procedures such as by chromatography, crystallization-recrystallization, and the like.

Procedures for preparing aracylimidazoles and acyl halide reactants used to form the compounds of this invention are known in the art. See, for example, R. B. Wagner and H. D. Zook, *Synthetic Organic Chemistry*, 1953, John Wiley & Sons, Chapter 17, page 546, et seq. The aracylimidazole can be prepared in situ by reacting carbonyldiimidazole with the appropriate phenylacetic acid of the formula

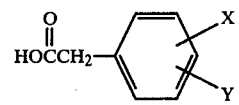

wherein X and Y are as defined above, in an organic solvent. Other carbodiimides such as dicyclohexylcarbodiimide can be used in place of the carbonyldiimidazole.

Exemplifying the aracylimidazole method, a solution of about 6.1 mmol of the selected phenylacetic acid and about 6.1 mmol of 1,1'-carbonyldiimidazole in about 43 ml of tetrahydrofuran are allowed to stand at room temperature for 3.5 hours. Then, a solution of about 6.1 mmol of the selected 4-aminomethyl-4-aminocyclohexanone, or ketal thereof in an inert solvent, e.g., about 13 ml of tetrahydrofuran, is added and the mixture is allowed to stand at room temperature for up to 50 hours, with at least occasional stirring or agitation. The solvent is then removed and the residue is dissolved in methylene chloride. The organic fraction, after basic pH and neutral conventional work-up, followed by concentration under vacuum, is dried. The residue is recrystallized yielding the desired acetamide derivative product of this invention.

Examples of compounds which have been made using the above method include:

(1) N-[[1-(dimethylamino)-4-oxocyclohex-1-yl]methyl]-2-(3,4-dichlorophenyl)acetamide ethylene ketal, m.p. 102°–105° C. (recrystallized from diethyl ether).

Anal. for $C_{19}H_{26}Cl_2N_2O_3$:
Calcd. C, 56.86; H, 6.53; N, 6.98; Found C, 56.70; H, 6.54; N, 6.82.

By formal nomenclature methods, this compound might be named 2-(3,4-dichlorophenyl)-N-[[8-(N,N-dimethylamino)-1,4-dioxaspiro[4.5]dec-8-yl]methyl-]acetamide;

(2) N-[[1-(dimethylamino)-4-oxocyclohex-1-yl]methyl]-2-(3,4-dichlorophenyl)acetamide propylene ketal, m.p. 149°–154° C. (recrystallized from a methylene chloride-Skellysolve ® B mixture).

Anal. for $C_{20}H_{28}Cl_2O_3$: Calcd. C. 57.83; H, 6.79; N, 6.75; Found C, 57.45; H, 6.87; N, 6.52.

By more formal nomenclature methods, this compound can be named 2-(3,4-dichlorophenyl)-N-[[9-(N,N-dimethylamino)-1,5-dioxaspiro[5.5]undec-9-yl]methyl]acetamide.

(3) N-[[1-(N-allyl-N-methylamino)-4-oxocyclohex-1-yl]methyl]-2-(3,4-dichlorophenyl)acetamide ethylene ketal, m.p. 71°–74° C. (recrystallized from diethyl ether).

Anal. for $C_{21}H_{28}Cl_2N_2O_3$: Calcd. C, 59.02; H, 6.60; N, 6.56; Found C, 59.11; H, 6.59; N, 6.56.

By another nomenclature method, this compound can be named 2-(3,4-dichlorophenyl)-N-[[8-(N-allyl-N-methylamino)-1,4-dioxaspiro[4.5]dec-8-yl]methyl-]acetamide.

(4) N-[[1-(N-pyrrolidinyl)-4-oxocyclohex-1-yl]methyl]-2-(3-bromo-4-methoxyphenyl)acetamide ethylene ketal as its hydriodic acid salt, m.p. 194°–195° C. (recrystallized from methylene chloride-ethyl acetate). By formal nomenclature methods, this compound can be named 2-(3-bromo-4-methoxyphenyl)-N-[[8-(1-pyrrolidinyl)-1,4-dioxaspiro-[4.5]dec-8-yl]methyl]acetamide.

Using the acid halide method, an ice-cooled solution of about 4.9 mmol of the selected 4-aminomethyl-4-aminocyclohexanone, or ketal thereof, and about 0.69 ml of triethylamine, or other equivalent trialkylamine, in an inert solvent such as 15 ml of tetrahydrofuran is treated with a solution of 5.0 mmol of the selected phenylacetyl chloride in 10 ml of tetrahydrofuran. After allowing the mixture to stand with or without agitation for about 18 hours in the cold (−10° to 10° C.—refrigerator overnight), the bulk of the solvent is removed under vacuum and the residue is dissolved in diethyl ether and washed with aqueous sodium bicarbonate solution. The aqueous fraction is extracted once with diethyl ether and the organic fractions are pooled and dried. The residue is recrystallized to yield the desired acetamide derivative product.

The starting 4-aminomethyl-4-aminocyclohexanone ketals can be prepared by reacting 4-oxocyclohexanone monoketal with potassium cyanide and the selected amine acid salt in a solvent such as methanol-water to form the respective 4-cyano-4-aminocyclohexanone ketal intermediate, wherein P and Q, taken together, complete an alkylenedioxy group, as defined above

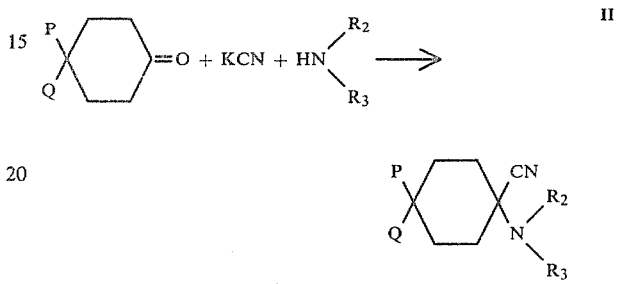

Compounds of formula I wherein R is $C_1$ to $C_3$-alkyl can be prepared by reacting the intermediate 4-cyano-4-aminocyclohexanone ketal (II) with the appropriate $C_1$ to $C_3$-alkyllithium reagent in an inert non-polar solvent (e.g., ether, benzene). Treatment of the intermediate imine with a reducing agent such as lithium aluminum hydride or sodium borohydride and the like, leads to 4-amino-4-amino(substituted)methyl cyclohexanone ketal which can then be converted to the amide of this invention with aracyl imidazole or acyl halide according to the general procedures given above.

Compounds of formula I wherein R and $R_1$ are both hydrogen are conveniently prepared when 4-cyano-4-aminocyclohexanone ketal (II) is subjected to a lithium aluminum hydride reduction in non-alcoholic, non-aqueous inert solvent such as diethyl ether at temperatures which may vary from about −78° C. to about 0° C. It is recommended that an ether solvent such as diethyl ether as opposed to a solvent such as tetrahydrofuran, at relatively low temperatures (below 0° C.), be used to avoid displacement of the cyano group in the preparation. When the reduction is complete, a basic work up of the reaction mixture with sodium hydroxide and water, which results in precipitation of the aluminum salts followed by taking the resultant filtrate to dryness gives the crude 4-aminomethyl-4-aminocyclohexanone ketal intermediates. These intermediates (II) can be further purified before reaction with the selected phenylacetic acid and carbonyl diimidazole or phenylacetyl chloride, but such purification is not necessary.

If the desired dialkylamine is not readily available, the intermediate 4-cyano-4-aminocyclohexanone ketal wherein $R_3$ is $C_1$ to $C_6$-alkyl can be prepared by an alternate route shown below:

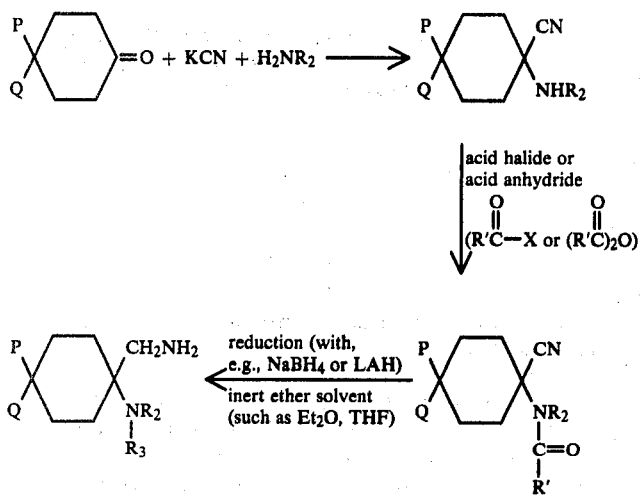

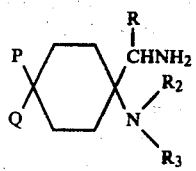

wherein P and Q, taken together, represent an alkylenedioxy group as defined above, $R_2$ is $C_1$ to $C_6$-alkyl, $R'$ is $R_3$-alkyl residue minus one carbon atom, so that $R'$ is H or $C_1$ to $C_5$-alkyl giving $R_3=1$ to 6 carbon atoms.

The reaction of secondary amine and potassium cyanide with the cyclohexanedione mono-ethylene ketal is preferred when the dialkylamine is available or can be readily prepared.

Compounds of formula I wherein $R_1$ is $C_1$ to $C_3$-alkyl can be prepared by methods known in the art. Two general methods which can be used are the following:

An intermediate of formula III (obtained as described above in general terms)

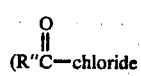   III is treated with an alkyl formate (HCOO alkyl) or an acid halide $$\underset{(R''\text{C--chloride}}{\overset{O}{\|}}$$

or bromide with R" being $CH_3$ or $C_2H_5$) to form an amide which can then be reduced to give the diamine of formula IV

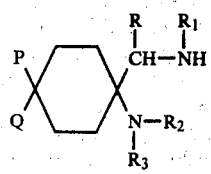   IV

This diamine IV then is a starting material used in the preparation of compounds of formula I wherein $R_1$ is $C_1$ to $C_3$-alkyl.

In an alternate method useful to prepare compounds of this invention wherein $R_1$ is $C_1$ to $C_3$-alkyl, i.e., a compound of the invention having a methyl, ethyl or propyl group on the amido nitrogen, the formula I compound wherein $R_1$ is hydrogen is dissolved in tetrahydrofuran or a similar non-polar solvent, the solution is cooled in ice and is treated with an organometallic base, such as butyl lithium, in pentane. After stirring the mixture in the cold for about 20 minutes, the required amount, i.e., at least a stoichiometrically equivalent amount, of the selected $C_1$ to $C_3$-alkyl iodide is added. The mixture is stirred at room temperature until reaction is complete, usually within about 20 hours. Then the resultant reaction mixture can be treated with saturated ammonium chloride in water solution. The organic layer is separated from the aqueous layer, diluted with benzene, and washed in turn with water and brine, and then evaporated to dryness. The resultant product ($R_1=C_1-C_3$-alkyl) can be purified by known procedures such as by column chromatography on Silica Gel ® using a solvent such as 3% methanol in chloroform. After the product is collected from the appropriate fractions it can be converted to its pharmacologically acceptable salt, e.g., to its hydrochloride.

EXAMPLE 1

Preparation of
2-(3,4-dichlorophenyl)-N-[[8-(1-pyrrolidinyl)-1,4-dioxaspiro[4.5]dec-8-yl]methyl]acetamide (a) Cyclohexane-1,4-dione, ethylene ketal A reaction mixture consisting of 10 gm (0.085 mole) 4-hydroxycyclohexanone, 4.75 ml ethylene glycol, 0.20 gm p-toluenesulfonic acid, and 100 ml benzene was heated at the reflux temperature in a reaction vessel fitted with a Dean and Stark trap for 2 hours. After the reaction mixture cooled, it was washed first with water and then with brine. The benzene was then removed by evaporation under reduced pressure giving the intermediate 4-hydroxycyclohexane mono-ketal as a viscous oil weighing 14.12 gm. The 4-hydroxycyclohexane mono-ketal was dissolved in 100 ml methylene chloride and added with stirring to a suspension consisting of 55.0 gm chromium trioxide (predried for 24 hours under reduced pressure over phosphorous pentoxide), one liter dry methylene chloride, 52.8 gm 3,5-dimethylpyrazole. After continued stirring for ten (10) minutes this dark reaction mixture was poured onto a two liter column of silica gel. When the reaction mixture had been completely absorbed, the chromatogram was developed with a 1:1 mixture of ethyl acetate and technical hexane (Skellysolve B—a mixture of isomeric hexanes having a boiling range between 60° and 70° C.). Fractions which were found by thin layer chromatography (TLC) to contain the product were collected and combined, after which the solvents were removed by evaporation under reduced pressure. The crystals thus obtained were recrystallized from technical hexane, and there was thus obtained 10.82 gm (91% yield) of the desired cyclohexane-1,4-dione, ethylene mono-ketal having a melting point at 68° to 69° C. (The literature value is 71.5° to 72.5° C.)

(b) 4-cyano-4-pyrrolidinocyclohexanone, ethylene ketal

To a mixture of 3 ml of methanol, 5.0 g of pyrrolidine and 20 ml of 2.5 N hydrochloric acid there was added in turn 3.0 g of potassium cyanide and 3.0 g (0.019 mol) of 1,4-cyclohexanedione, mono-ethylene ketal. The mixture was stirred at room temperature for 24 hours and then extracted thoroughly with methylene chloride. The combined extracts were taken to dryness and the residue recrystallized with petroleum ether to yield 3.78 g (84%) of the subtitled product, m.p., 46°-50° C.

(c) 4-aminomethyl-4-pyrrolidinocyclohexanone, ethylene ketal

To a stirred suspension of 0.17 g of lithium aluminum hydride in 3 ml of diethyl ether, cooled in a dry ice-acetone bath there was added a solution of 0.50 g (2.12 mmol) of the 4-cyano-4-pyrrolidinocyclohexanone ethylene ketal [from part (b) above] in 11 ml of diethyl ether over a period of 15 minutes. The mixture was stirred in the cold for 1 hour following addition, and at room temperature for 3 hours. The resultant mixture was then cooled in an ice bath and to the mixture was added in turn 0.17 ml of water, 0.17 ml of 15 percent sodium hydroxide solution, and 0.51 ml of water. The resultant inorganic gel was collected on a filter and rinsed twice with diethyl ether. The filtrate was taken to dryness to yield 0.54 g of a crystalline solid which was recrystallized from a diethyl ether-petroleum ether mixture. There was obtained 0.24 g of the subtitled solid, m.p., 71°-73° C.

Anal. for $C_{13}H_{24}N_2O_2$:
Calcd. C, 64.96; H, 10.06; N, 11.66;
Found C, 64.72; H, 9.80; N, 11.61.

(d) 2-(3,4-dichlorophenyl)-N-[[8-(1-pyrrolidinyl)-1,4-dioxaspiro[4.5]dec-8-yl]methyl]acetamide To a solution of 3.28 g (0.016 mol) of 3,4-dichlorophenylacetic acid in 35 ml of tetrahydrofuran (THF) was added 2.59 g of carbonyldiimidazole. The mixture was stirred at room temperature for 4 hours, following which time a solution of 3.61 g (16 mmol) of the diamine (prepared as in part (c) above) in 65 ml of THF was added to it all at once. After stirring the solution at room temperature the solvent (THF) was removed under reduced pressure. The residue was dissolved in diethyl ether and this organic layer was washed with water, aqueous sodium bicarbonate, water, and was dried. The resulting solution was evaporated to dryness and the residue was crystallized and recrystallized from an ethyl acetate-Skellysolve B ® mixture to give the subtitled acetamide product, m.p., 125°-127° C. (40% yield). The mass spectrum for this product is in accord with the assigned structure.

Anal. for $C_{12}H_{28}Cl_2N_2O_3$:
Calcd. C, 59.02; H, 6.60; N, 6.56;
Found C, 59.02; H, 6.76; N, 6.53.

If it is desired to form the 4-oxo formula 1 compound (P+Q is O=), such can be obtained by refluxing the ketal form of the product of this invention (P+Q is

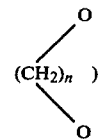

in an aqueous mineral acid-methanol solution overnight, or until the ketal group is hydrolyzed to the ketone group.

The 4-oxo compounds of this invention (P+Q is O=) can be used as intermediates for the preparation of compounds of the formula 1 above, wherein one of P or Q is hydroxy (OH) and the other of P or Q is hydrogen, $C_1$ to $C_3$-alkyl, or phenyl-$C_1$ to $C_2$-alkyl, and wherein R, $R_1$, $R_2$, $R_3$, X and Y are as defined above.

Compounds wherein P or Q is hydrogen can be prepared by reduction using known procedures, e.g., with sodium borohydride in alcohol. See also, for example, E. L. Eliel and D. Nasipuri, *J. Org. Chem.*, 30, 3809 (1965).

Compounds wherein P or Q is alkyl or phenyl-$C_1$ to $C_2$-alkyl can be prepared by reacting the ketone with the appropriate alkyl or phenylalkylgrignard reagent (prepared in the conventional manner from alkyl or phenylalkyl halide and magnesium) in an inert solvent such as tetrahydrofuran, under an inert atmosphere such as nitrogen gas. Such procedures are well known in the chemical art—see, for example, Fieser and Fieser, *Reagents for Organic Synthesis, Vol.* 1, John Wiley, N.Y., 1967, p 419 ff.

When reaction of an amide, such as I, wherein $R_1$ is hydrogen and P and Q taken together represent an oxo group with a Grignard reagent leads to formation of an insoluble magnesium salt, it is advantageous to use an additional base, such as an alkyllithium, in order to maintain the reactant in solution and thus facilitate the addition reaction of the Grignard reagent to the ketone functionality.

Generally, the ketone is placed in a solvent such as tetrahydrofuran under an inert atmosphere such as nitrogen gas and is cooled, e.g., in a dry ice-acetone bath; butyllithium in pentane is added while the ketone-solvent mixture is stirred. Subsequently, the cooled stirred solution is treated with a Grignard reagent, e.g., methyl magnesium bromide or benzylmagnesium chloride, or the like, in a non-polar solvent, e.g., diethyl ether. The mixture can be stirred until reaction is essentially complete, e.g., at room temperature for about one-half to three days, and is then treated with saturated ammonium chloride in water solution. After conventional aqueous work up and drying, the resultant 4-hydroxy-4-P-1-amino-1-amidomethylcyclohexane residue can be purified by column chromatography.

Compounds which can be prepared as described immediately above include:
2-(3,4-dichlorophenyl)-N-[[4-hydroxy-4-methyl-1-(1-pyrrolidinyl)cyclohex-1-yl]methyl]acetamide, from the product of Example 1, which is deketalized under acidic conditions, followed by reaction with methylgrignard, e.g., methylmagnesium bromide, in THF, and work up;

2-(3,4-dichlorophenyl)-N-[[4-hydroxy-4-benzyl-1-dimethylaminocyclohex-1-yl]methyl]acetamide from the 4-oxo form of the compound in listed Examples 1 and 2 above, and benzyl Grignard, e.g., benzylmagnesium chloride, in THF, and work up.

Other compounds wherein the 1-amino and 1-amido residues are varied can be made similarly from the appropriate 4-oxo starting materials, which, in turn, are derivable from the 4-ketal compounds by acidic hydrolysis. These 4-hydroxy compounds are new and have analgesic properties in standard tests.

The compounds of this invention (I) or their acid addition salts in their crystalline state may be isolated as solvates, i.e., with a discrete quantity of solvent, e.g., water, ethyl acetate, ethanol, and the like, associated physically, and thus removable without effective alteration of the chemical entity per se. Examples of acid addition salts which may be made from the compounds of this invention include those from hydrochloric, methanesulfonic, p-toluenesulfic, hydrobromic, sulfuric, acetic, oxalic, cyclohexanesulfamic, succinic, $\beta$-naphthalenesulfonic, maleic, fumaric, citric, lactic, pamoic acids and the like. Acid addition salts can be prepared by reacting a formula I free base with a stoichiometric amount of the desired acid, either neat or in aqueous or organic liquid non-aqueous solvent media such as diethyl ether, ethyl acetate, and the like. Non-aqueous media are preferred. Also, whereas oxalic acid can be used to get the formula I product into a more easily handled solid form, it would preferably not be used as a pharmacologically acceptable salt form of the formula I product.

The compounds wherein P and Q are dissimilar substituents can exist in cis and trans conformations with respect to substituents in positions 1 and 4 on the cyclohexane. Also, chirality exists at the 1-methylene carbon ($\alpha$ to the cyclohexyl ring) when R is alkyl of 1 to 3 carbon atoms. Resolution can be effected if desired by known racemic mixture separation procedures. The compound scope included in this invention is not intended to be limited to any particular conformational or optical isomer form.

The term "$C_1$ to $C_3$-alkyl," as used herein, means a methyl, ethyl, propyl or an isopropyl group. The term "$C_1$ to $C_6$-alkyl" means the above $C_1$ to $C_3$-alkyl groups as well as the normal and isomeric forms of butyl, pentyl and hexyl groups. The term "$C_3$ to $C_5$-allylic alkenyl" means 2-propenyl (allyl), 2-butenyl, 2-pentenyl, 3-methyl-2-butenyl, 4-methyl-2-butenyl, and the like. The term "halogen having at atomic number of from 9 to 35" means fluorine, chlorine or bromine.

This invention also relates to compositions containing a formula I compound as an active ingredient in a pharmaceutical carrier. The compositions are useful in pharmaceutical dosage unit forms of the formula I compounds for systemic administration (oral, rectal and parenteral administration form) in therapy for treating and alleviating pain in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity of the essential active ingredient compound of this invention calculated to produce the desired effect, in combination with the required pharmaceutical means which adapt the said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these aminoamide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 250 mg of the essential active ingredient per dosage unit form not to exceed about 250 mg per day; the preferred dosage is 2–150 mg per day, which, as aforesaid, may be in the form of a semi-solid or solid, oral, or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic and narcotic antagonist effects within the aforesaid effective non-toxic range. Expressed otherwise, when used systemically, an amount of the essential active ingredient is provided to a recipient within a range from about 0.01 mg per kg to about 4 mg per kg of body weight of the recipient depending upon the age, weight, condition of the patient or other factors of concern to the physician. Preferred dosages for most applications are 0.03 to 1.5 mg per kg of body weight.

The useful pharmaceutical dosages unit forms of these compounds in pharmaceutical formulations is preferably adapted for systemic administration to obtain analgesic and narcotic antagonist effects comprising an effective, non-toxic amount of a compound according to formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systematically to the mammals the aforesaid pharmaceutical dosage unit forms supplying an effective, non-toxic amount for analgesic and narcotic antagonist effects. These compounds have an advantage, to a greater extent, depending upon the particular compound, of having lower physical dependence liability than known analgesic compounds such as morphine and methadone, as shown by evaluation of representative compounds and those standard analgesic drug compounds in various pharmacological test procedures which measure relative degrees of analgesic and the physical dependence liability of the test compounds in standard laboratory test animals.

Representative examples of these formula I compounds have $ED_{50}$ values of less than about 75 mg/kg s.c. (subcutaneous administration) in standard laboratory animal analgesic tests such as the tail flick, pinch, and writhing tests, and the more potent of them have $ED_{50}$ values of less than 10 mg/kg (s.c.) in these tests, while at the same time giving quite high values (greater than 90 mg/kg s.c.) in the naloxone jumping test thus possessing only low to moderate apparent physical dependence liability as compared to commercial analgesics used as standards. The procedures used to determine these properties of these new compounds were essentially those of Way, et al, (Way, E. L., et al, "Simultaneous Quantitative Assessment of Morphine Tolerance and Physical Dependence", *K. Pharmacol, Exp. Ther.*, 167, pp 1–8 (1969) and Saalens, et al, (Saalens, J. K., et al, "The Mouse Jumping Test—A Simple Screening Method to Estimate the Physical Dependence Capacity of Analgesics," *Arch. Int. Pharmacodyn.*, 190, pp 213–218 (1971). Statistical effective doses ($ED_{50}$ values) and 95% confidence limits were calculated by the method of Spearman and Karber (Finney, D. J., "Statistical Methods in Biological Assay," Hafner Publ., (1952).

For example, representative preferred compounds of formula I give low analgesic $ED_{50}$ values (less than about 10 mg of test compound/kg of animal body weight, subcutaneous administration route) in standard laboratory animal tests while at the same time possessing quite high $ED_{50}$ values (greater than 250 mg/kg in s.c.) in the naxolone jumping test, evidencing substantial freedom from apparent physical dependence liability. In contrast, known analgesic drugs such as morphine and methadone exhibit analgesic $ED_{50}$ values of less than 2 mg/kg, s.c., in these standard analgesic tail flick, pinch, and writhing tests, but are known to have high apparent physical dependence liability effects, and this is confirmed by their (morphine and methadone) having relatively low naloxone jumping $Ed_{50}$ values ranging from 12 to 30 mg/kg s.c. Also, the known compound, 3,4,-dichloro-N-[[1-(N, N-dimethylamino)cyclohex-1-yl]methyl]benzamide which has analgesic $ED_{50}$ values ranging from 0.5 to 1 mg/kg in these standard animal tests, also has a naxolone jumping test $ED_{50}$ of about 12 mg/kg, similar to morphine and methadone. Although other representative compounds of this invention have analgesic potencies somewhat less than the preferred compounds (analgesic activity $ED_{50}$ values up to about 70 mg/kg s.c., in these standard tests) they still are characterized by having only low to moderate apparent physical dependence liability.

Although not necessary in the embodiments of the inventive concept, additional active ingredients can be incorporated in the present pharmaceutical dosage unit forms as desired. For example, each pharmaceutical dosage unit form may contain therein an amount within the following non-toxic effective ranges: tranquilizers, anti-psychotic and anti-anxiety agents, such as chlorpromazine (5 to 50 mg). thioridazine (5 to 200 mg), haloperidol (0.5 to 5 mg), meprobamate (100 to 400 mg), chlordiazepoxide (5 to 50 mg), diazepam (2 to 15 mg), triazolam (25 to 1 mg), ketazolam (5 to 300 mg), and ectylurea (100 to 300 mg); barbiturates such as phenobarbital (8 to 60 mg), butabarbital (8 to 60 mg), and amobarbital (16 to 120 mg); analgesics, anti-pyretics and anti-inflammatories, such as aspirin (150 to 600 mg), flurbiprofen (20 to 200 mg), ibuprofen (2 to 400 mg), naproxen (20 to 200 mg), indomethacin (20 to 200 mg) and acetaminophen (150 to 600 mg); and anti-depressants, such as amitriptyline hydrochloride (10 to 50 mg), methylphenidate hydrochloride (5 to 20 mg), d-amphetamine (5 to 20 mg), d-amphetamine sulfate (2 to 15 mg), methamphetamine hydrochloride (2 to 15 mg), depending upon the condition being treated.

EXAMPLE 2

A sterile aqueous suspension suitable for intramuscular injection and containing in each milliliter 25 mg of 2-(3,4-dichlorophenyl)-N-[[8-(1-pyrrolidinyl)-1,4-dioxaspiro[4.5]dec-8-yl]methyl]acetamide as the essential active ingredient is prepared from the following ingredients:

| | | |
|---|---|---|
| Essential active ingredient | 2.5 | g |
| Polyethylene glycol 4000, U.S.P. | 3 | g |
| Sodium chloride | 0.9 | g |
| Polysorbate 80, U.S.P. | 0.4 | g |
| Sodium metabisulfite | 0.1 | g |
| Methylparaben, U.S.P. | 0.18 | g |
| Propylparaben, U.S.P. | 0.02 | g |
| Water for injection, q.s. to | 100 | ml |

The preceding sterile injectable is useful in the treatment of pain at a dose of ½ to 2 ml.

EXAMPLE 3

One thousand tablets for oral use, each containing 40 mg of N-[[1-(dimethylamino)-4-oxocyclohex-1-yl]methyl]-2-(3,4-dichlorophenyl)acetamide propylene ketal as the essential active ingredient are prepared from the following ingredients:

| | | |
|---|---|---|
| Essential active ingredient | 40 | g |
| Dicalcium phosphate | 150 | g |
| Methylcellulose, U.S.P. (15 cps) | 6.5 | g |
| Talc | 20 | g |
| Calcium Stearate | 2.0 | g |

The essential active ingredient and dicalcium phosphate are mixed well, granulated with 7.5% aqueous solution of methylcellulose, passed through a No. 8 screen and dried carefully. The dried granules are passed through No. 12 screen, mixed with the talc and stearate and compressed into tablets. These tablets are useful in the treatment of pain in adult humans at a dose of 1 tablet one to four times a day, as needed.

EXAMPLE 4

One thousand 2-piece hard gelatin capsules for oral use, each capsule containing 20 mg of 2-(3,4-dichlorophenyl)-N-[[8-(1-pyrrolidinyl)-1,4-dioxaspiro-[4.5]dec-8-yl]methyl]acetamide as the essential active ingredient are prepared from the following ingredients:

| | |
|---|---|
| Essential active ingredient | 20 g |
| Lactose, U.S.P. | 100 g |
| Starch, U.S.P. | 10 g |
| Talc, U.S.P. | 5 g |
| Calcium Stearate | 1 g |

The finely powdered materials are mixed thoroughly, then filled into hard gelatin capsules of appropriate size.

One capsule 4 times a day is useful for the treatment of pain in adult humans.

EXAMPLE 5

One-piece soft elastic capsules for oral use, each containing 100 mg of 2-(3-bromo-4-methoxyphenyl)-N-[[8-(1-pyrrolidinyl)-1,4-dioxaspiro[4.5]dec-8-yl]methyl]acetamide as the essential active ingredient are prepared in the usual manner by first dispersing the powdered active material in sufficent corn oil to render the material capsulatable.

One capsule 2 times a day is useful in the treatment of pain in adult humans.

EXAMPLE 6

An aqueous oral preparation containing in each teaspoonful (5 ml) 50 mg of N-[[1-(dimethylamino)-4-oxocyclohex-1-yl]methyl]-2-(3,4-dichlorophenyl)acetamide, propylene ketal as the essential active ingredient is prepared from the following ingredients:

| | |
|---|---|
| Essential active ingredient | 100 g |
| Methylparaben, U.S.P. | 7.5 g |
| Propylparaben, U.S.P. | 2.5 g |
| Saccharin Sodium | 12.5 g |
| Glycerin | 3,000 g |
| Tragacanth powder | 10 g |
| Orange oil flavor | 10 g |
| Orange II | 7.5 g |
| Deionized water, q.s. to | 10,000 ml |

The foregoing aqueous preparation is useful in the treatment of adult pain at a dose of 1 teaspoonful 4 times a day.

EXAMPLE 7

One thousand suppositories, each weighing 2.5 gm and containing 75 mg of 2-(3,4-dichlorophenyl)-N-[[8-(1-pyrrolidinyl)-1,4-dioxaspiro[4.5]dec-8-yl]methyl]acetamide, as the active ingredient, are prepared from the following ingredients:

| | |
|---|---|
| Essential active ingredient | 75 gm |

-continued

| | |
|---|---|
| Propylene glycol | 165 gm |
| Polyethylene glycol 4000 q.s. | 2,500 gm |

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of post-surgical pain at a dose of one suppository rectally twice a day.

The following examples illustrate pharmaceutical compositions containing the aminoamide compounds of this invention in combination with other drug compounds.

EXAMPLE 8

One thousand tablets for oral administration, each containing 10 mg of 2-(3,4-dichlorophenyl)-N-[[8-(1-pyrrolidinyl)-1,4-dioxaspiro[4.5]dec-8-yl]methyl]acetamide, as the essential active ingredient and 16.2 mg of phenobarbital are prepared from the following ingredients:

| | | |
|---|---|---|
| Essential active ingredient, micronized | 10 | g |
| Phenobarbital | 16.2 | g |
| Lactose | 150 | g |
| Starch | 15 | g |
| Magnesium Stearate | 1.5 | g |

The ingredients are thoroughly mixed and slugged. The slugs are broken down by forcing through a screen and the resulting granules are then compressed into tablets.

These tablets are useful in reducing post-surgical pain in dogs at a dose of 1 to 3 tablets depending on the weight of the animal and its condition.

EXAMPLE 9

One thousand hard gelatin capsules for oral use, each containing 10 mg of 2-(3,4-dichlorophenyl)-N-[[8-(1-pyrrolidinyl)-1,4-dioxaspiro[4.5]dec-8-yl]methyl]acetamide as the essential active ingredient and 40 mg ketazolam are prepared from the following ingredients:

| | | |
|---|---|---|
| Essential active ingredient, micronized | 10 | g |
| Ketazolam | 40 | g |
| Starch | 125 | g |
| Talc | 25 | g |
| Magnesium Stearate | 1.5 | g |

One capsule 4 times a day is useful in the relief of pain in adult humans.

EXAMPLE 10

Ten thousand scored tablets for oral use, each containing 30 mg of 2-(3,4-dichlorophenyl)-N-[[8-(1-pyrrolidinyl)-1,4-dioxaspiro[4.5]dec-8-yl]methyl]acetamide as the essential active ingredient and 32 mg of caffeine are prepared from the following ingredients:

| | |
|---|---|
| Essential active ingredient, micronized | 300 g |

| -continued | |
|---|---|
| Caffeine | 320 g |
| Lactose | 1,500 g |
| Corn Starch | 500 g |
| Talc | 500 g |
| Calcium Stearate | 25 g |

The ingredients are thoroughly mixed and slugged. The slugs are broken down by forcing through a number 16 screen. The resulting granules are then compressed into tablets each containing 30 mg of the acetamide essential active ingredient and 32 mg of caffeine.

The combination of active materials is effective in reducing pain in adult humans. The dose is one-half of two tablets 3 times a day, depending on the severity of the condition.

EXAMPLE 11

Ten thousand tablets for oral use, each containing 60 mg of N-[[1-(dimethylamino)-4-oxocyclohex-1-yl]methyl]-2-(3,4-dichlorophenyl)acetamide propylene ketal as the essential active ingredient and 0.5 mg of methylprednisolone are prepared from the following ingredients using the procedure described in Example 8.

| Essential active ingredient, | |
|---|---|
| micronized | 600 g |
| Methylprednisolone | 5 g |
| Lactose | 1,000 g |
| Corn Starch | 500 g |
| Talc | 500 g |
| Calcium Stearate | 25 g |

These tablets are useful in treating adult humans suffering from arthritic pain by administering one tablet 3 times a day.

EXAMPLE 12

Ten thousand tablets for oral use, each containing 5 mg of 2-(3,4-dichlorophenyl)-N-[[8-(1-pyrrolidinyl)-1,4-dioxaspiro[4.5]dec-8-yl]methyl]acetamide as the essential active ingredient and 320 mg acetaminophen, are prepared from the following ingredients and using the procedure of Example 8.

| Essential active ingredient, | |
|---|---|
| finely powdered | 50 g |
| Acetaminophen, finely powdered | 3,200 g |
| Corn Starch | 500 g |
| Talc | 500 g |
| Calcium Stearate | 50 g |

This tablet is useful in treating homotopic pain or headache in an adult patient by administering one or two tablets 3 times a day depending on the severity of the condition.

In similar formulations the acetaminophen can separately be replaced by aspirin (320 mg/tablet) or Phenacetin-Aspirin-Caffeine (P-A-C) compound (390 mg/tablet).

EXAMPLE 13

One thousand tablets for oral use, each containing 80 mg of 2-(3-bromo-4-methoxyphenyl)-N-[[8-(1-pyrrolidinyl)-1,4-dioxaspiro[4.5]dec-8-yl]methyl]acetamide as the essential active ingredient and 400 mg of chlorophenes in carbamate (Maolate) are prepared from the following ingredients:

| Essential active ingredient, | | |
|---|---|---|
| micronized (the maleate salt) | 95 | g |
| Maolate | 400 | g |
| Lactose | 50 | g |
| Starch | 15 | g |
| Magnesium Stearate | 1.5 | g |

The ingredients are thoroughly mixed and slugged. The slugs are broken down by forcing through a screen and the resulting granules are then compressed into tablets.

These tablets are useful in reducing pain and muscle spasms at a dose of one tablet 1 to 3 times per day, depending upon the severity of the condition.

EXAMPLES 14–26

Following the procedures of the preceding Examples 2 to 13, inclusive, similar dosage forms of other formula I compounds can be prepared by substituting an equivalent amount of the following compounds as the essential active ingredient, for example:

(14) 2-(3,4-dichlorophenyl)-N-[[8-(N-methyl-N-butyl)-1,4-dioxaspiro[4.5]dec-8-yl]methyl]acetamide

(15) 2-(3,4-dichlorophenyl)-N-methyl-N-[[8-(N-methyl-N-butyl)-1,4-dioxaspiro[4.5]dec-8-yl]methyl]-acetamide

(16) 2-(3,4-dichlorophenyl)-N-[[1-(1-pyrrolidinyl)-4-oxocyclohex-1-yl]methyl]acetamide

(17) 2-(3,4-dibromophenyl)-N-[[8-(dipropylamino)-1,4-dioxaspiro[4.5]dec-8-yl]methyl]acetamide

(18) 2-(4-azidophenyl)-N-[[9-(N-methyl-N-ethylamino)-1,5-dioxaspiro[5.5]undec-9-yl]methyl]acetamide

(19) 2-(3-trifluoromethylphenyl)-N-methyl-N-[[8-(dimethylamino)-1,4-dioxaspiro[4.5]dec-8-yl]methyl]acetamide

(20) 2-(3-chloro-4-methylphenyl)-N-[α-[8-(dimethylamino)-1,4-dioxaspiro[4.5[dec-8-yl]ethyl]acetamide

(21) 2-(3-trifluoromethylphenyl)-N-[[8-(1-pyrrolidinyl)-1,4-dioxaspiro[4.5]dec-8-yl]methyl]acetamide

(22) 2-(2,4-difluorophenyl)-N-[[1-(1-pyrrolidinyl)-4-oxocyclohex-1-yl]methyl]acetamide

(23) 2-(4-methoxy-3-methyl)-N-[[8-(N-methyl-N-butylamino)-1,4-dioxaspiro[4.5]dec-8-yl]methyl]acetamide

(24) 2-(3,4-dichlorophenyl)-N-[[8-(diethylamino)-1,4-dioxaspiro[4.5]dec-8-yl]methyl]acetamide

(25) 2-(3,4-dichlorophenyl)-N-[[1-(1-pyrrolidinyl)-4-hydroxy-4-benzylcyclohex-1-yl]methyl]acetamide

(26) 2-(3,4-dichlorophenyl)-N-[(1-dimethylamino-4-benzyl-4-hydroxycyclohex-1-yl)methyl]acetamide.

We claim:

1. A compound of the formula

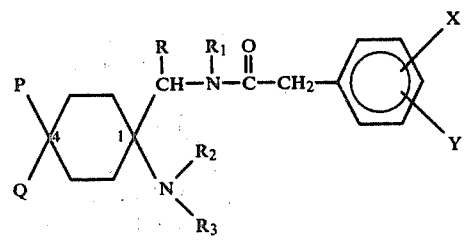

wherein
- R is hydrogen or $C_1$ to $C_3$-alkyl;
- $R_1$ is hydrogen or $C_1$ to $C_3$-alkyl;
- each of $R_2$ and $R_3$ is independently a $C_1$ to $C_6$-alkyl, or $R_2$ is a $C_3$ to $C_5$-(allylic)alkenyl when $R_3$ is a $C_1$ to $C_6$-alkyl, or $R_2$ and $R_3$, taken together with the nitrogen to which they are bonded complete a mono-nitrogen heterocyclic ring having 3 to 4 carbon atoms;
- Q and P, taken together, represent an oxo group (O=) or a $C_2$ to $C_3$-alkylenedioxy group; taken separately, when P or Q is hydroxy, then the other of P or Q is hydrogen, $C_1$ to $C_3$-alkyl or phenyl-($C_1$ to $C_2$)alkyl;
- each of X and Y is selected from the group consisting of hydrogen, $C_1$ to $C_3$-alkyl, $C_1$ to $C_3$-alkyloxy, a halogen having an atomic number of from 9 to 35, nitro, trifluoromethyl and azido, providing that when X is halogen, Y is $C_1$ to $C_3$-alkyl, $C_1$ to $C_3$-alkyloxy or halogen, and that when X is nitro, trifluoromethyl or azido, Y is hydrogen, and the pharmacologically acceptable salts thereof.

2. A compound according to claim 1 wherein R is hydrogen, $R_1$ is hydrogen, $R_2$ and $R_3$ are taken together with the nitrogen to which they are bonded to complete a mono-nitrogen heterocyclic ring having from 3 to 4 carbon atoms; Q and P are taken together to complete a $C_2$ to $C_3$-alkylenedioxy group, and
- X and Y are halogens having an atomic number of from 9 to 35, and the pharmacologically acceptable salts thereof.

3. A compound according to claim 2 wherein the compound is 2-(3,4-dichlorophenyl)-N-[[8-(1-pyrrolidinyl)-1,4-dioxaspiro[4.5]dec-8-yl]methyl]acetamide, and the pharmacologically acceptable salts thereof.

4. A compound according to claim 1 wherein R is hydrogen, $R_1$ is hydrogen, each of $R_2$ and $R_3$ is $C_1$ to $C_6$-alkyl, P and Q are taken together to complete a $C_2$ to $C_3$-alkylenedioxy group, and
- each of X and Y is a halogen having an atomic number of from 9 to 35, and the pharmacologically acceptable salts thereof.

5. A compound according to claim 4 wherein the compound is 2-(3,4-dichlorophenyl)-N-[[8-(N,N-dimethylamino)-1,4-dioxaspiro[4.5]dec-8-yl]-methyl]acetamide, and the pharmacologically acceptable salts thereof.

6. A compound according to claim 4 wherein the compound is 2-(3,4-dichlorophenyl)-N-[[9-(N,N-dimethylamino)-1,5-dioxaspiro[5.5]undec-9-yl]methyl]acetamide, and the pharmacologically acceptable salts thereof.

7. A compound according to claim 1 wherein R is hydrogen, $R_1$ is hydrogen, $R_2$ is a $C_3$ to $C_5$-(allylic)alkenyl, $R_3$ is $C_1$ to $C_6$-alkyl, P and Q are taken together to complete a $C_2$ to $C_3$-alkylenedioxy group, and X and Y are each halogens having an atomic number of from 9 to 35, and the pharmacologically acceptable salts thereof.

8. A compound according to claim 7 wherein the compound is N-[[8-(N-allyl-N-methylamino)-1,4-dioxaspiro[4.5]dec-8-yl]methyl]-2-(3,4-dichlorophenyl)acetamide, and the pharamacologically acceptable salts thereof.

9. A compound according to claim 1 wherein R is hydrogen, $R_1$ is hydrogen, $R_2$ and $R_3$ are taken together with the nitrogen to which they are bonded to complete a mono-nitrogen heterocyclic ring containing 3 to 4 carbon atoms, P and Q are taken together to complete a $C_2$ to $C_3$-alkylenedioxy group, X is a halogen having an atomic number of from 9 to 35, and Y is a $C_1$ to $C_3$-alkyloxy group, and the pharmacologically acceptable salts thereof.

10. A compound according to claim 9 wherein the compound is 2-(3-bromo-4-methoxyphenyl)-N-[[8-(1-pyrrolidinyl)-1,4-dioxaspiro[4.5]dec-8-yl]methyl]acetamide, and the pharmacologically acceptable salts thereof.

11. A compound according to claim 1 wherein R is hydrogen, $R_1$ is hydrogen, each of $R_2$ and $R_3$ is $C_1$ to $C_6$-alkyl, P is hydroxy and Q is phenyl-$C_1$ to $C_2$-alkyl, and each of X and Y is a halogen having an atomic number of from 9 to 35, and the pharmocologically acceptable salts thereof.

12. A compound according to claim 11 wherein the compound is 2-(3,4-dichlorophenyl)-N-[[1-(dimethylamino)-4-hydroxy-4-benzycyclohex-1-yl]methyl]acetamide, and the pharmacologically acceptable salts thereof.

13. A composition useful in pharmaceutical dosage unit form for alleviating pain in warm-blooded mammals which comprises a compound of formula 1 in claim 1 in combination with a pharmaceutically acceptable carrier.

14. A composition according to claim 13 wherein the essential active ingredient for alleviating pain is a compound according to claim 2.

15. A composition according to claim 14 wherein the essential active pain-alleviating ingredient is a compound according to claim 3.

16. A method for alleviating pain which comprises administering to a warm-blooded mammal a pain-alleviating effective amount of a compound of formula I in claim 1 in a pharmaceutical dosage unit form.

17. A method according to claim 16 wherein the pain-alleviating compound is a compound according to claim 2.

18. A method according to claim 17 wherein the pain-alleviating compound is a compound according to claim 3.

* * * * *